US007753856B2

(12) United States Patent
Dziubinski

(10) Patent No.: US 7,753,856 B2
(45) Date of Patent: Jul. 13, 2010

(54) METHOD, DEVICE AND SYSTEM FOR CARDIO-ACOUSTIC SIGNAL ANALYSIS

(75) Inventor: Marek Dziubinski, Warsaw (PL)

(73) Assignee: Medicalgorithmics Ltd., Warsaw (PL)

( * ) Notice: Subject to any disclaimer, the term of this patent is extended or adjusted under 35 U.S.C. 154(b) by 114 days.

(21) Appl. No.: 12/102,470

(22) Filed: Apr. 14, 2008

(65) Prior Publication Data

US 2008/0260173 A1    Oct. 23, 2008

Related U.S. Application Data

(63) Continuation-in-part of application No. 12/090,183, filed on Feb. 3, 2009, which is a continuation of application No. PCT/PL2006/000068, filed on Oct. 16, 2006.

(60) Provisional application No. 60/987,192, filed on Nov. 12, 2007, provisional application No. 60/987,180, filed on Nov. 12, 2007, provisional application No. 60/987,043, filed on Nov. 10, 2007, provisional application No. 60/986,761, filed on Nov. 9, 2007, provisional application No. 60/956,782, filed on Aug. 20, 2007, provisional application No. 60/948,527, filed on Jul. 9, 2007.

(30) Foreign Application Priority Data

Oct. 14, 2005   (EP)   ................... 05077368
Sep. 2, 2007    (PL)   ..................... 383243

(51) Int. Cl.
*A61B 7/00*    (2006.01)
(52) U.S. Cl. ........................ 600/528; 600/463; 600/480; 600/450; 600/514
(58) Field of Classification Search .................. 600/528, 600/480, 450, 463, 514; 128/699–670
See application file for complete search history.

(56) References Cited

U.S. PATENT DOCUMENTS 4,356,486 A    10/1982   Mount (Continued)

FOREIGN PATENT DOCUMENTS

EP    1 473 667 A2    3/2004

(Continued)

OTHER PUBLICATIONS

E. Zwicker et al., "Audio Engineering and Psychoacoustics: Matching Signals to the Final Receiver, the Human auditory System," Journal of the Audio Engineering Society, vol. 39, No. 3, Mar. 1, 1991, pp. 115-126.

(Continued)

*Primary Examiner*—Carl H Layno
*Assistant Examiner*—Paula J Stice
(74) *Attorney, Agent, or Firm*—Pierce Atwood LLP; Joseph M. Maraia; Christopher E. Everett

(57) ABSTRACT

A method for cardio-acoustic signal analysis includes receiving a signal representative of heart sounds and displaying the signal in a time-perceptual frequency-perceptual loudness domain representation. The received signal is transformed to represent a time-perceptual frequency-amplitude domain. The method further includes applying a human auditory modeling algorithm to the time-perceptual frequency-amplitude domain representation to generate the time-perceptual frequency-perceptual loudness domain representation.

18 Claims, 12 Drawing Sheets

U.S. PATENT DOCUMENTS

| | | | |
|---|---|---|---|
| 4,407,288 A | 10/1983 | Langer et al. | |
| 4,572,182 A | 2/1986 | Royse | |
| 4,622,979 A | 11/1986 | Katchis et al. | |
| 4,763,663 A | 8/1988 | Uphold et al. | |
| 4,803,625 A | 2/1989 | Fu et al. | |
| 4,889,131 A | 12/1989 | Salem et al. | |
| 4,916,441 A | 4/1990 | Gombrich | |
| 4,938,228 A | 7/1990 | Righter et al. | |
| 4,958,641 A | 9/1990 | Digby et al. | |
| 4,967,756 A | 11/1990 | Hewitt | |
| 4,977,899 A | 12/1990 | Digby et al. | |
| 5,003,984 A | 4/1991 | Muraki et al. | |
| 5,012,814 A | 5/1991 | Mills et al. | |
| 5,012,815 A * | 5/1991 | Bennett et al. | 600/528 |
| 5,024,225 A | 6/1991 | Fang | |
| 5,033,474 A | 7/1991 | Varelis et al. | |
| 5,111,396 A | 5/1992 | Mills et al. | |
| 5,128,552 A | 7/1992 | Fang et al. | |
| 5,191,891 A | 3/1993 | Righter | |
| 5,226,425 A | 7/1993 | Righter | |
| 5,238,001 A | 8/1993 | Gallant et al. | |
| D341,659 S | 11/1993 | Homayoun et al. | |
| 5,289,824 A | 3/1994 | Mills et al. | |
| 5,304,186 A | 4/1994 | Semler et al. | |
| 5,307,818 A | 5/1994 | Segalowitz | |
| 5,317,269 A | 5/1994 | Mills et al. | |
| 5,319,363 A | 6/1994 | Welch et al. | |
| 5,333,616 A | 8/1994 | Mills et al. | |
| 5,351,695 A | 10/1994 | Mills et al. | |
| 5,365,935 A | 11/1994 | Righter et al. | |
| 5,381,804 A | 1/1995 | Shambroom | |
| 5,417,222 A | 5/1995 | Dempsey et al. | |
| 5,441,047 A | 8/1995 | David et al. | |
| 5,467,773 A | 11/1995 | Bergelson et al. | |
| D372,785 S | 8/1996 | Sabri et al. | |
| 5,573,506 A | 11/1996 | Vasko | |
| 5,581,369 A | 12/1996 | Righter et al. | |
| D377,983 S | 2/1997 | Sabri et al. | |
| 5,630,710 A | 5/1997 | Tune et al. | |
| 5,631,495 A | 5/1997 | Dunn et al. | |
| 5,687,717 A | 11/1997 | Halpern et al. | |
| 5,704,364 A | 1/1998 | Saltzstein et al. | |
| 5,730,143 A | 3/1998 | Schwarzberg | |
| 5,749,367 A | 5/1998 | Gamlyn et al. | |
| 5,752,976 A | 5/1998 | Duffin et al. | |
| 5,819,007 A | 10/1998 | Elghazzawi | |
| 5,885,245 A | 3/1999 | Lynch et al. | |
| 5,931,791 A | 8/1999 | Saltzstein et al. | |
| 5,941,829 A | 8/1999 | Saltzstein et al. | |
| 5,959,529 A | 9/1999 | Kail, IV | |
| D414,870 S | 10/1999 | Saltzstein et al. | |
| D427,315 S | 6/2000 | Saltzstein et al. | |
| D429,336 S | 8/2000 | Francis et al. | |
| 6,171,237 B1 | 1/2001 | Avitall et al. | |
| 6,225,901 B1 | 5/2001 | Kail, IV | |
| 6,366,871 B1 | 4/2002 | Geva | |
| 6,466,806 B1 | 10/2002 | Geva et al. | |
| 6,486,779 B1 | 11/2002 | Alroy | |
| 6,537,233 B1 * | 3/2003 | Rangayyan et al. | 600/586 |
| 6,569,095 B2 | 5/2003 | Eggers | |
| 6,664,893 B1 | 12/2003 | Eveland et al. | |
| 6,665,385 B2 | 12/2003 | Rogers et al. | |
| 6,694,177 B2 | 2/2004 | Eggers et al. | |
| 6,801,137 B2 | 10/2004 | Eggers | |
| 6,871,089 B2 | 3/2005 | Korzinov et al. | |
| 6,940,403 B2 | 9/2005 | Kail | |
| 6,957,107 B2 | 10/2005 | Rogers et al. | |
| 7,002,468 B2 | 2/2006 | Eveland et al. | |
| 7,099,715 B2 | 8/2006 | Korzinov et al. | |
| 7,130,396 B2 | 10/2006 | Rogers et al. | |
| 7,194,300 B2 | 3/2007 | Korzinov | |
| 7,212,850 B2 | 5/2007 | Prystowsky et al. | |
| 7,222,054 B2 | 5/2007 | Geva | |
| 7,266,405 B1 | 9/2007 | Alroy et al. | |
| 7,299,159 B2 | 11/2007 | Nanikashvili | |
| 7,374,545 B2 | 5/2008 | Alroy | |
| 2002/0032387 A1 | 3/2002 | Geva et al. | |
| 2002/0067256 A1 | 6/2002 | Kail | |
| 2003/0028442 A1 | 2/2003 | Wagstaff et al. | |
| 2003/0176795 A1 | 9/2003 | Harris et al. | |
| 2003/0187363 A1 | 10/2003 | Alroy | |
| 2004/0260189 A1 | 12/2004 | Eggers et al. | |
| 2005/0119580 A1 | 6/2005 | Eveland | |
| 2005/0171448 A1 | 8/2005 | Korzinov et al. | |
| 2005/0203349 A1 | 9/2005 | Nanikashvili | |
| 2005/0222515 A1 | 10/2005 | Polyshchuk et al. | |
| 2006/0084881 A1 | 4/2006 | Korzinov | |
| 2006/0155203 A1 * | 7/2006 | Munk | 600/528 |
| 2007/0015973 A1 | 1/2007 | Nanikashvili | |
| 2007/0129642 A1 | 6/2007 | Korzinov | |
| 2007/0130657 A1 | 6/2007 | Rogers et al. | |
| 2007/0156054 A1 | 7/2007 | Korzinov et al. | |
| 2007/0219453 A1 | 9/2007 | Kremliovsky et al. | |
| 2007/0288067 A1 | 12/2007 | Eveland | |
| 2007/0293776 A1 | 12/2007 | Korzinov et al. | |

FOREIGN PATENT DOCUMENTS

| | | |
|---|---|---|
| WO | WO-93/22970 | 11/1993 |
| WO | WO-01/93758 A1 | 12/2001 |
| WO | WO 2004/032742 A | 4/2004 |
| WO | WO-2005/006209 A1 | 1/2005 |
| WO | WO 2007/043902 A | 4/2007 |

OTHER PUBLICATIONS

M. Brusco et al., "Digital phonocardiography: a PDA-based approach," 26th Annual International Conference of the IEEE Engineering in Medicine and Biology Society, vol. 3, 2004, pp. 229-2302.

R. Erickson et al., "In-vitro study of mechanical heart valve sound loudness as measured by ISO-532/B," 1994 Proceeding of IEEE Seventh Symposium on Computer-Based Medical Systems, 1994, pp. 53-54.

PCT International Search Report—PCT/PL2006/000067 Dated of Mailing Jun. 21, 2007.

PCT International Search Report—PCT/PL2006 /000068 Date of Mailing Feb. 26, 2007.

Krishna Prasad G et al: "Classification of ECG Arrhythmias using Multi-Resolution Analysis and Neural Networks" IEEE TENCON 2003—Conference on Technologies for the Asia-Pacific Region—vol. IV, Oct. 15-17, 2003 Bangalore, India: pp. 227-231.

European Search Report—(EP 08 15 9995) Date of Mailing Oct. 7, 2008.

* cited by examiner

METHOD, DEVICE AND SYSTEM FOR CARDIO-ACOUSTIC SIGNAL ANALYSIS

RELATED APPLICATIONS

This application claims the benefit of U.S. Provisional Application No. 60/956,782, filed on Aug. 20, 2007 and is a continuation of International Application No. PCT/PL2006/000067 filed on Oct. 16, 2006, published in English, which claims priority under 35 U.S.C. §119 or 365 to EP Application No. 05077367.0, filed Oct. 14, 2005, the entire teachings of the above applications are incorporated herein by reference. This application is a continuation-in-part of U.S. application Ser. No. 12/090,183, filed on Apr. 14, 2008, which claims the benefit of U.S. Provisional Application No. 60/987,192, filed on Nov. 12, 2007, U.S. Provisional Application No. 60/987,180, filed on Nov. 12, 2007, U.S. Provisional Application No. 60/987,043, filed on Nov. 10, 2007, U.S. Provisional Application No. 60/986,761, filed on Nov. 9, 2007, Polish Patent Application No. P 383243, filed on Sep. 2, 2007, entitled "A system for remote cardiac rehabilitation" (English translation), U.S. Provisional Application No. 60/948,527, filed on Jul. 9, 2007, and is a continuation of International Application No. PCT/PL2006/000068, filed on Oct. 16, 2006, published in English, which claims priority under 35 U.S.C. §119 or 365 to EP Application No. 05077368.8. filed Oct. 14, 2005, the entire teachings of the above applications are incorporated herein by reference.

BACKGROUND

Heart (cardiac) auscultation is a very old technique, which is still commonly used during medical examinations carried out by physicians. It is performed using a standard non-electronic stethoscope, an electronic analogue stethoscope or a modern digital stethoscope. Cardiac auscultation is based on auditory perception of sounds produced by the heart in certain areas of the human body. These sounds are often accompanied by special kind of maneuvers which enhance some significant sounds, clicks or murmurs produced by the heart muscle and the blood flow across heart valves. Cardiac auscultation is difficult to perform properly due to the limitations of human hearing.

A cardiac auscultation examination requires nearly perfect hearing and extensive experience of a physician in dealing with rare cases of heart abnormalities. However, while experience increases with age, hearing deteriorates. Furthermore, acoustic signals have very (low) small amplitude and a heart's activity is usually represented by very low frequencies which remain on the edge of human perception. Also, pathologies detectable via cardiac auscultation are rare, and therefore physicians are not able to compare various cases representative of a given pathology thereby making diagnosis even more difficult. That is, an ordinary physician usually does not have enough experience to determine the audible phenomena, e.g. whether the extra sounds, murmurs or clicks are pathological, or not.

Additionally, interpretation of the results of an auscultation exam is very subjective, because different doctors have different experience and hearing abilities. Cardiac auscultation also requires very good hearing, which is not very common among human population (while it is necessary to perform cardiac auscultation effectively). Since hearing and experience of each human being differ, result of the auscultation is often very subjective matter. Hence, in many cases Cardiac auscultation is not treated seriously among medical community despite its potential. For this reason, despite its potential, cardiac auscultation is treated as a preliminary overview of the patient's heart condition, rather than a source of reliable information for potential treatment.

SUMMARY

Phonocardiography is the best known technology, which aids physicians in dealing with heart sounds. It is based on visualization of the time domain acoustic cardiac signal. The general idea of this technology has been adopted from the ECG analysis, where the time domain electrophysiological waveform is analyzed by a medical specialist. However such approach is not appropriate for acoustic signals, because listening to the signal differs from viewing the time domain waveform, especially since acoustic events may happen simultaneously at different frequencies. Physicians have tried to see in the waveform what should be heard (since the extensive cardiac auscultation knowledge, gathered over nearly 200 years, describes the acoustical phenomena), which turned out to be not very effective approach. For this reason phonocardiography was and still is rejected by the medical community.

Phonocardiography may be improved by multi-band analysis, where several waveforms related to specific sub-bands are filtered out and often processed in a non-linear fashion. Such improvements allow physicians to identify acoustic events related to different frequencies. However, this approach is still insufficient due to nonlinear complexity of sound perception.

Alternative methods of cardiac auscultation signal processing are based on simulating human auditory system. In those methods the time domain waveform is represented as a 3 dimensional surface (digital image—time-frequency-amplitude map) where changes of the amplitude over time, for certain frequencies can be observed. The human auditory system functions in a similar manner, i.e. a listener detects energy of certain acoustic events and is able to determine their frequency and the moment of their occurrence. For example, one can notice that at certain time high frequency click occurred and after some time low frequency-clatter was present, etc.

However, these methods do not accurately represent the nonlinear character of the human auditory system and therefore do not properly show what should be heard (but still are closer to simulating human hearing than phonocardiography). It is due to the fact that human auditory system operates with specific frequency resolution, which is very high for lower frequencies and decreases with the increase of the sounds frequency.

Additionally, some acoustic events are inaudible, when they occur in direct presence (in time and/or frequency) of louder events. This phenomenon is known as perceptual masking and is used for example in MPEG audio coding standard (i.e. in the popular MP3). Furthermore, loudness of certain acoustic events is not directly related to their amplitude (energy), i.e. some frequencies are heard better than others and consequently some cannot be heard at all (usually sounds below 20 Hz and above 20 kHz.

In general the methods described above are based on mathematical signal transformations, which convert the time domain waveform into frequency domain. They are usually based on methods such as DFT (Discrete Fourier Transform), DWT (Discrete Wavelet Transform—wavelet spectrum), CWT (Complex Wavelet Transform) and several other techniques with some nonlinear enhancements, which however, do not take into account complexity of the human auditory system.

An alternative technology (alternative examination) to cardiac auscultation is so called heart ECHO (USG or ultrasound of the heart). This method enables a physician to determine a valves performance and allows for detecting other pathologies of the heart muscle. This examination, however, is expensive and requires highly trained medical personnel. Therefore, providing a reliable alternative to standard cardiac auscultation could be beneficial for a patient and is economically justified since allows for avoiding unnecessary and expensive ECHO.

Further, an electrocardiogram (ECG) is a graphic produced by an electrocardiograph, which records the electrical activity of the heart over time. Analysis of the various waves and normal vectors of depolarization and repolarization yields important diagnostic information. The ECG does not allow a physician to detect heart valve pathologies because these pathologies do not correspond with electrical activity of the heart muscle.

There is provided a method and system for performing cardio-acoustic signal analysis. The method includes receiving a signal representative of heart sounds and displaying the signal in a time-perceptual frequency-perceptual loudness domain representation. The method further can include transforming the received signal to represent a time-perceptual frequency-amplitude domain.

In some embodiments, the method can further include applying a human auditory system modeling algorithm to the time-perceptual frequency-amplitude domain representation to generate a time-perceptual frequency-perceptual loudness domain representation.

In some embodiments, the transformation can be based on inner products calculations using at least complex numbered impulse response filter banks representing a non-linear frequency resolution character. The complex numbered impulse response can represent properties of perceptual frequency characteristics. The perceptual frequency characteristics can include at least Bark units and mel scale. The complex numbered impulse response can allow for calculating phase (and amplitude) prediction of the representation components.

In some embodiments, the method can include calculating tonality using an unpredictability measure parameter. The method can also include distinguishing between noisy and tonal components in the signal. The method can further simulate periodicity perception.

In some embodiments, the method can include interpreting the time-perceptual frequency-perceptual loudness domain representation. The interpreting the time-perceptual frequency-perceptual loudness domain representation can include comparing the time-perceptual frequency-perceptual loudness domain representation to a perceived acoustical phenomena.

In some embodiments, the signal can be representative of at least cardiac auscultation and pulmonary auscultation. The method can further include applying periodicity analysis methods to the time-perceptual frequency-perceptual loudness domain representation. The method can further detect S1 and S2 of at least 2 cardiac cycles for calculating an averaged representation. The method can also limit influence of noise and other non-repetitive parasite artifacts and disturbances to the signal. The method can restore the cardiac auscultation signal.

A system for cardio-acoustic signal analysis includes an input sensor for receiving a signal representative of heart sounds and a display device for displaying the signal in a time-perceptual frequency-perceptual loudness domain representation. The system can further include a transformation module for transforming the received signal to represent a time-perceptual frequency-amplitude domain.

The system and methods presented herein provide the following advantages. These include, but are not limited to, visualization of the signal exactly as it should be heard by an ideal listener; allows a physician to utilize knowledge directly related to cardiac auscultation gathered for last 200 years by thousands of physicians; objectified analysis, i.e., the same signal always will result in the same representation and interpretation, which is not always possible if the same signal is heard by different people (since they may have different hearing abilities and listening experience); and objectified analysis of the artificial valve's performance where ECHO performs poorly and is not very reliable.

BRIEF DESCRIPTION OF THE DRAWINGS

The foregoing and other objects, features and advantages will be apparent from the following more particular description of the embodiments, as illustrated in the accompanying drawings in which like reference characters refer to the same parts throughout the different views. The drawings are not necessarily to scale, emphasis instead being placed upon illustrating the principles of the embodiments.

DESCRIPTION

In general, psychoacoustics (human auditory system modeling) is based on humans perceive sounds in terms of their amplitudes, frequencies, and time localization. Sounds of the same amplitudes, but different frequencies may be perceived as differently loud. Amplitude differences between sounds are frequency dependent, i.e. loudness relation between sounds of different frequencies varies with accordance to their energy. Quiet sounds may be masked (made inaudible) by louder sounds (maskers). This phenomenon depends on time and frequency distance between masked sounds and maskers. Perception of frequencies is non-linear, i.e. resolution of human auditory system is much higher for lower sounds, than for higher sounds. Noisy (chaotic) and periodic (tonal) components of the sounds are perceived differently.

Humans, while listening to the heart auscultation sounds, are able to focus on repetitive events, while some random events may be "separated" and disregarded. This innovation is based on a method of transforming the time domain waveform into the time—perceptual frequency—perceptual loudness domain. Such representation is obtained with regard to the mathematical model of the human auditory system.

Additionally, a set of algorithms responsible for simulating periodicity perception (pattern tracking) of acoustic events, i.e. humans are able to concentrate their attention on repetitive events (rhythmic events such as heart beat), rejecting incidental events, which usually are parasite disturbances.

Further, based on a periodicity analysis (pattern tracking and pattern tracking recovery); the auscultation signal may be significantly enhanced. Disturbing noise and parasite impulsive clicks of non-repetitive type may be removed, resulting in restored time domain representation of the auscultation sound.

Figure 1:
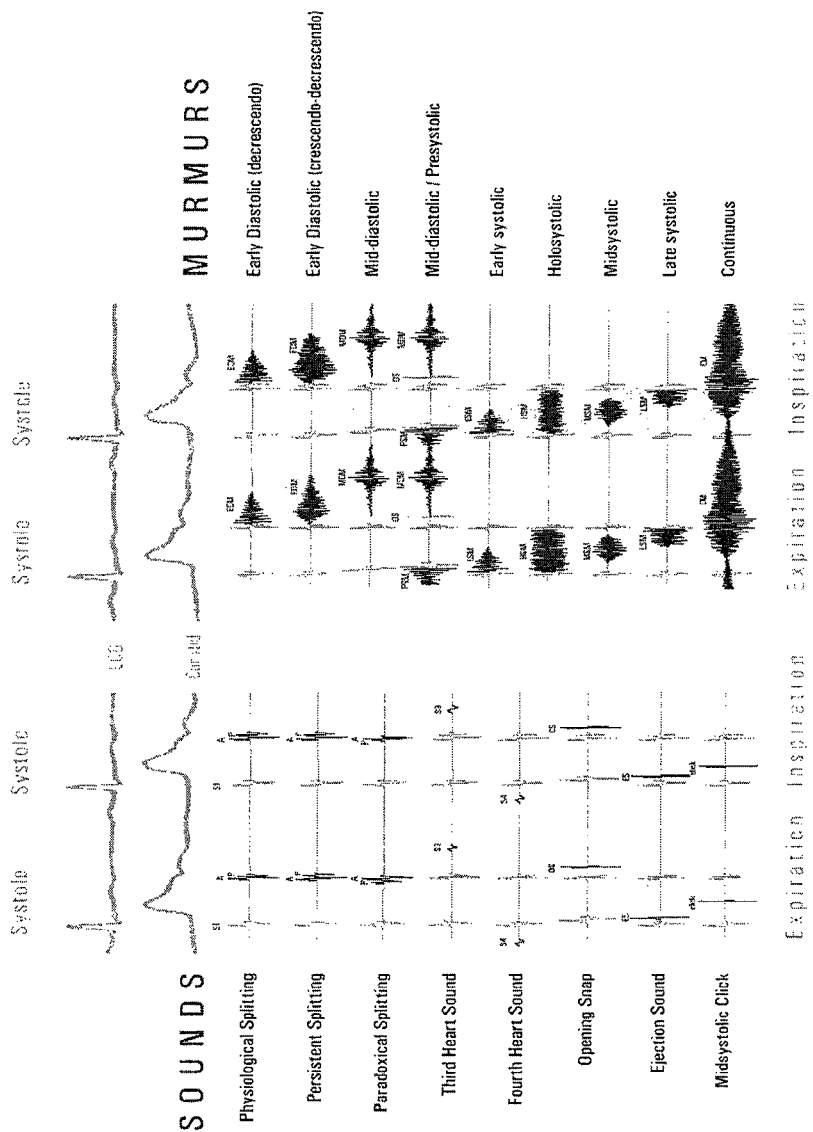
FIG. 1 shows graphical representations of acoustical phenomena that can be heard during cardiac auscultation.

FIG. 1 shows time domain graphical representations of acoustical phenomena that can be heard during cardiac auscultation. A standard cardiac stethoscope examination enables a doctor/physician to detect heart dysfunctions related to blood flow through the heart, such as heart valves dysfunctions. For example, valves leakiness (i.e. regurgitation) or improper (not complete) opening of the valve (i.e. stenosis). Cardiac auscultation is also commonly used to monitor the performance of artificial (implanted) mechanical valves, which tend to seal after some time and may require replacement. Also, presence of the extra sounds (S3 and S4) may be useful in detecting hemodynamic evidence of heart failure.

Figure 2:
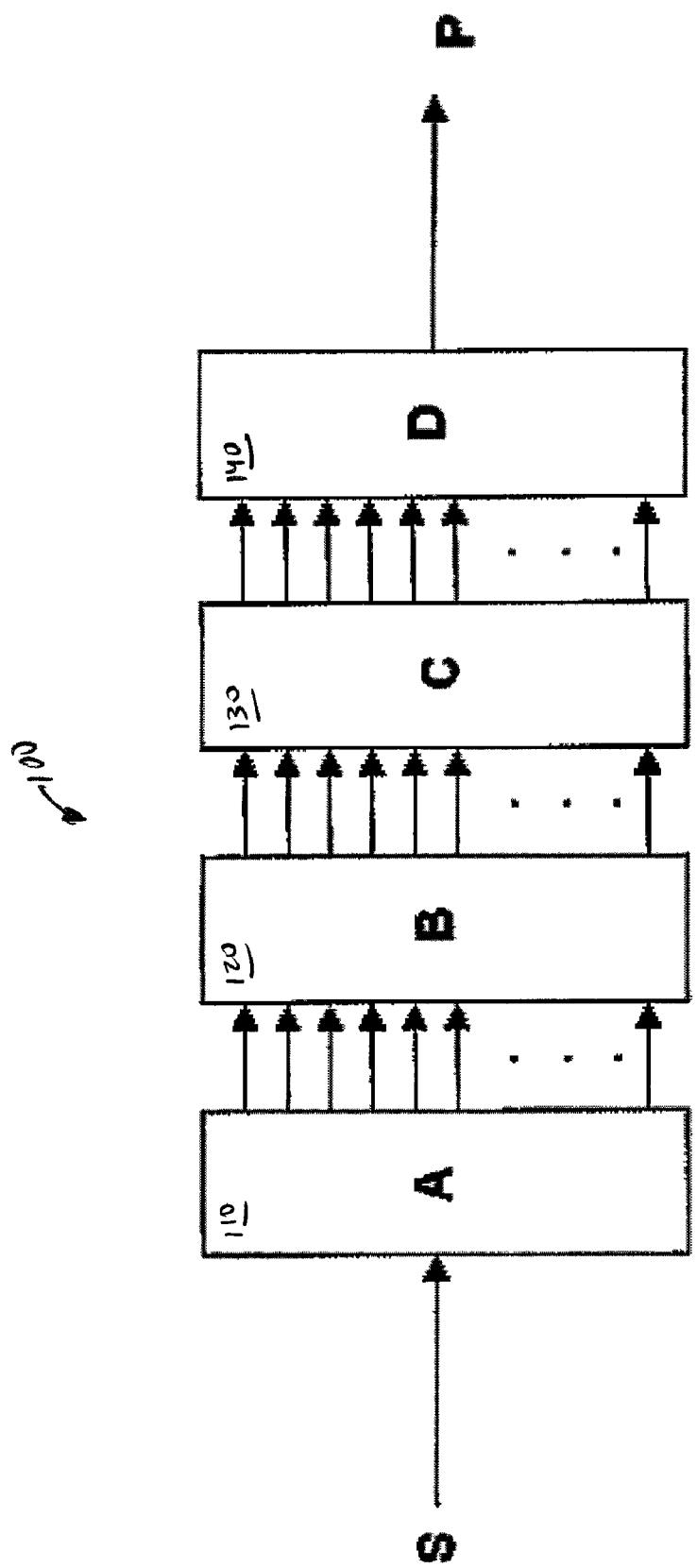
FIG. 2 is a schematic illustration of a system for performing cardio-acoustic signal analysis.

FIG. 2 is a schematic illustration of a system 100 for performing cardio-acoustic signal analysis. The system includes a digital input acoustic sensor 110, a psychoacoustic spectral transformation module 120, a Basiliar membrane excitation simulation module 130, and a psychoacoustic representation matrix module 140. Signal "S" represents a digital input acoustic sensor signal representative of heart sounds (time domain waveform), which is stored in an appropriate matrix and used as an input to the digital input acoustic sensor 110. The digital input acoustic sensor 100 signal is subject to segmentation, i.e. the digital input acoustic sensor signal is divided into shorter blocks of equal length. A matrix of the time domain short blocks becomes an input signal to the psychoacoustic spectral transformation module 120 where each time domain segment is transformed into a psychoacoustic spectral representation. Such representation is calculated with the use of inner products operations with regard to Bark units, i.e. frequency domain is represented by equally spaced spectral bins, however equal spacing refers to Bark units, thus such approach significantly differs from standard FFT, DWT, CWT, etc. The resulting representation vectors (each representing the input time domain blocks) is stored in an appropriate matrix and becomes input of to the Basiliar membrane excitation simulation module 130, which is responsible for simulating Basiliar membrane excitation and simultaneous masking phenomenon, i.e. total excitation is constructed of precise modeling of particular the membrane excitations.

A matrix constructed with the calculated Basiliar membrane deformation vectors becomes input to the psychoacoustic representation matrix module 140. The psychoacoustic representation matrix module 140 is responsible for simulating time domain Basiliar membrane behavior (time domain masking phenomenon), i.e. this method models the shape changes of the membrane over time. An output signal "P" from the psychoacoustic representation matrix module 140 is a matrix built from Basiliar membrane shapes, thus P is a psychoacoustic representation (in the form of the 3D map) in time-perceptual frequency-perceptual loudness domain.

Figure 3:
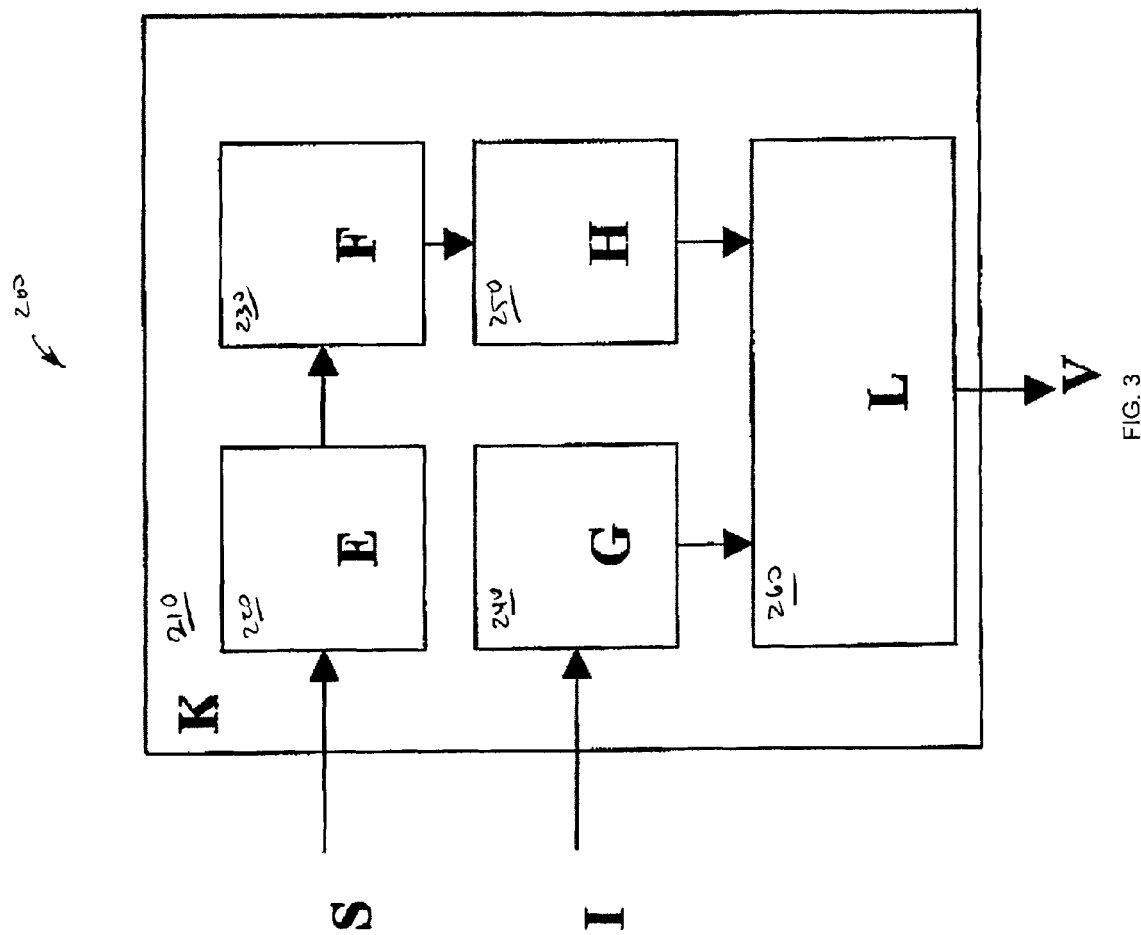
FIG. 3 is a schematic illustration of a device for performing cardio-acoustic signal analysis.

FIG. 3 is a schematic illustration of a device 200 for performing cardio-acoustic signal analysis, where the device 200 may be for example incorporated into a microprocessor module 210. The microprocessor module includes a signal storage and pre-processing module 220, a psychoacoustic representation module 230, a detector 240, a cardiac auscultation module 250, and a cardiac events detection module 260.

The signal storage and pre-processing module 220 receives a digital input acoustic sensor signal "S" representative of heart sounds (in time domain waveform). The signal storage and pre-processing module 220 is responsible for selecting a fragment of the input signal of 10 seconds duration. The chosen fragment is the most periodic part of the input signal, while periodicity indicator is obtained with the use of cross correlation algorithm applied for RMS envelope of the digital input acoustic sensor signal "S".

The psychoacoustic representation module 230 is responsible for calculating psychoacoustic representation (in time-perceptual frequency-perceptual loudness domain), as described with reference to FIG. 2. The output signal from the psychoacoustic representation module 230 is further processed in the cardiac auscultation module 250. The cardiac auscultation module 250 is a cardiac auscultation expert system (where parameterization of the examination information takes place).

Simultaneously, the periodicity detector 240 (simulating human perception of repetitive events versus incidental events), is responsible for processing of examination information (i.e. body position, auscultation area, inhalation/exhalation).

Such information is considered in determining significance of certain cardiac events, such as clicks and murmurs, which may be increased or decreased, depending on the body position, exhalation or inhalation or may not be present for certain auscultation areas. Output signals from the cardiac auscultation module 250 and the periodicity detector 240 are in the cardiac events detection module 260. After such processing, an output signal "V" of the cardiac events detection module 260 represents final results in the form of ascultatory findings.

Figure 4:
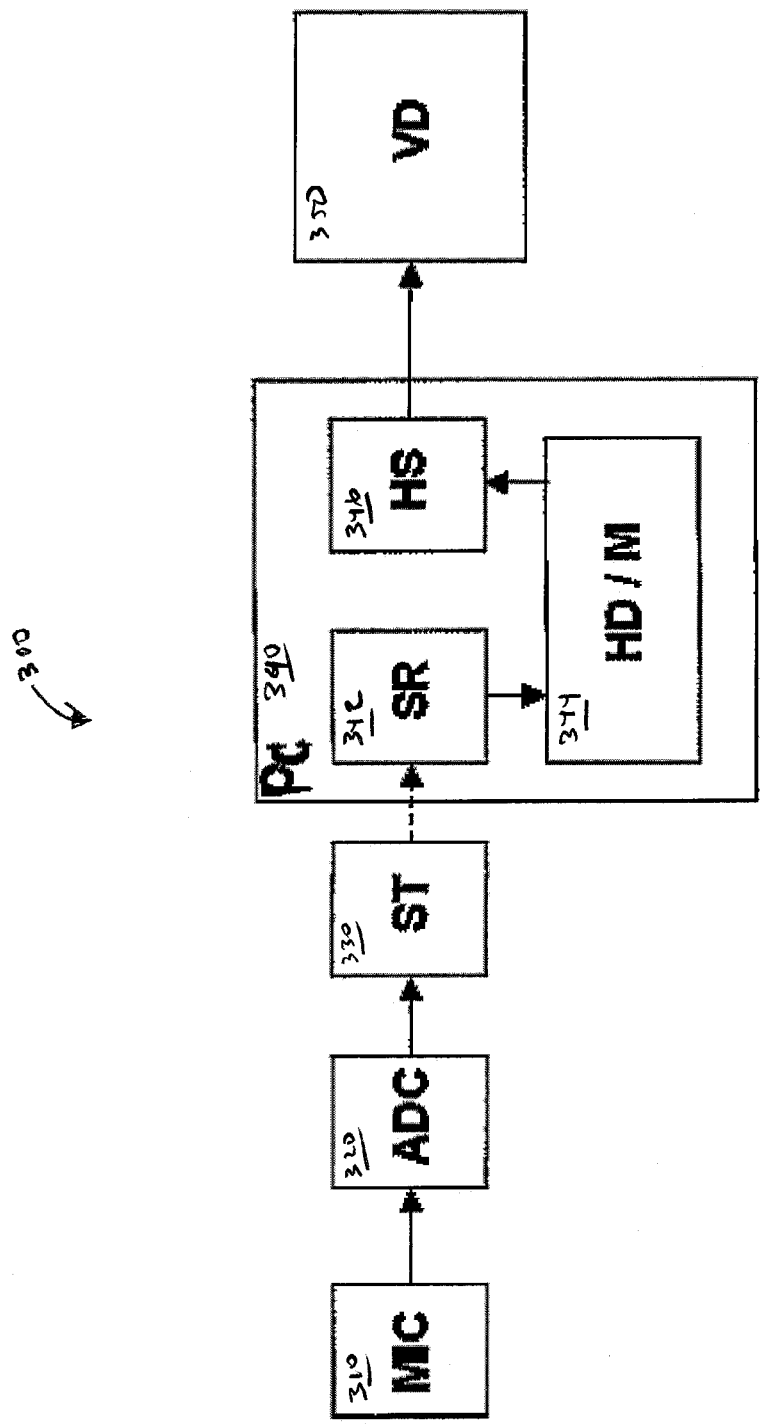
FIG. 4 is a schematic illustration of another system embodiment for performing cardio-acoustic signal analysis.

FIG. 4 is a schematic illustration of another system embodiment 300 for performing cardio-acoustic signal analysis. The system 300 includes a microphone 310, a analog-to-digital (A/D) converter 320, a signal radio/wire transmitter 330, a processing unit 340, and a visualization unit VD 350.

The microphone 310 is responsible for converting acoustic pressure changes into voltage changes. The A/D converter 320 converts a analogue (voltage changes signal) into an equally spaced digital signal. The signal radio/wire transmitter 330 is responsible for sending the digital signal to the processing unit (e.g. a computer) 340. In some embodiments, transmission can be carried out via a USB cable, a wireless transmitter, or the like. In some embodiments, the processing unit 340 can be a personal computer, a personal digital assistant, a device based digital signal processor chip, or the like. In some embodiments, the visualization unit 350 can be a standard monitor, an LCD display, or the like and is responsible for enabling data presentation to a user.

The processing unit 340 includes a signal receiver 342, a data storage device 344, and a microprocessor 346. In some embodiments, the signal receiver 342 can be a USB adapter for the use with a USB connection, or a radio receiver for the use with a radio transmission. The microprocessor 346 is described in with reference to FIG. 2. In some embodiments, the data storage device 344 can be a hard drive, random access memory, or the like.

Figure 5:
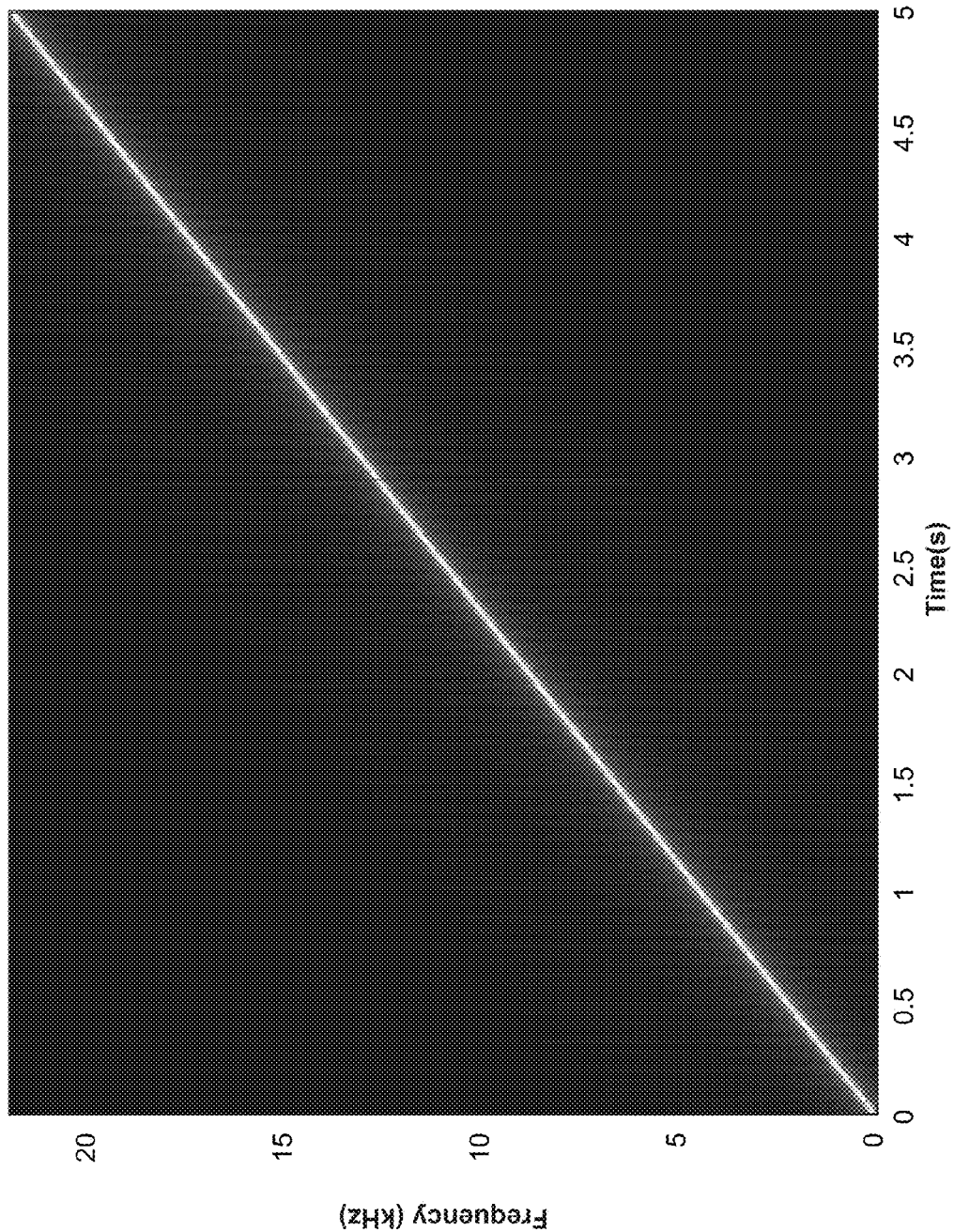
FIG. 5 represents a standard spectrogram.

FIG. 5 represents a standard spectrogram, i.e. time-frequency-amplitude map based on a short term DFT, where the signal is divided into short segments and Fourier spectra are calculated for all of the segments, forming columns of the image (matrix). FIG. 5 shows a sinusoidal signal spectrogram with linearly increasing frequency and constant amplitude (a "chirp signal"). The signal frequency evolves over 5 seconds from 0 Hz at the beginning to 22050 Hz at the end (fifth second). The black color of the map (image) represents minimum energy, while the white color represents maximum energy. The chirp signal is the white line starting from the bottom left corner of the image. The constant amplitude over time (and frequency) of the chirp signal is indicated by a constant white color.

Figure 6:
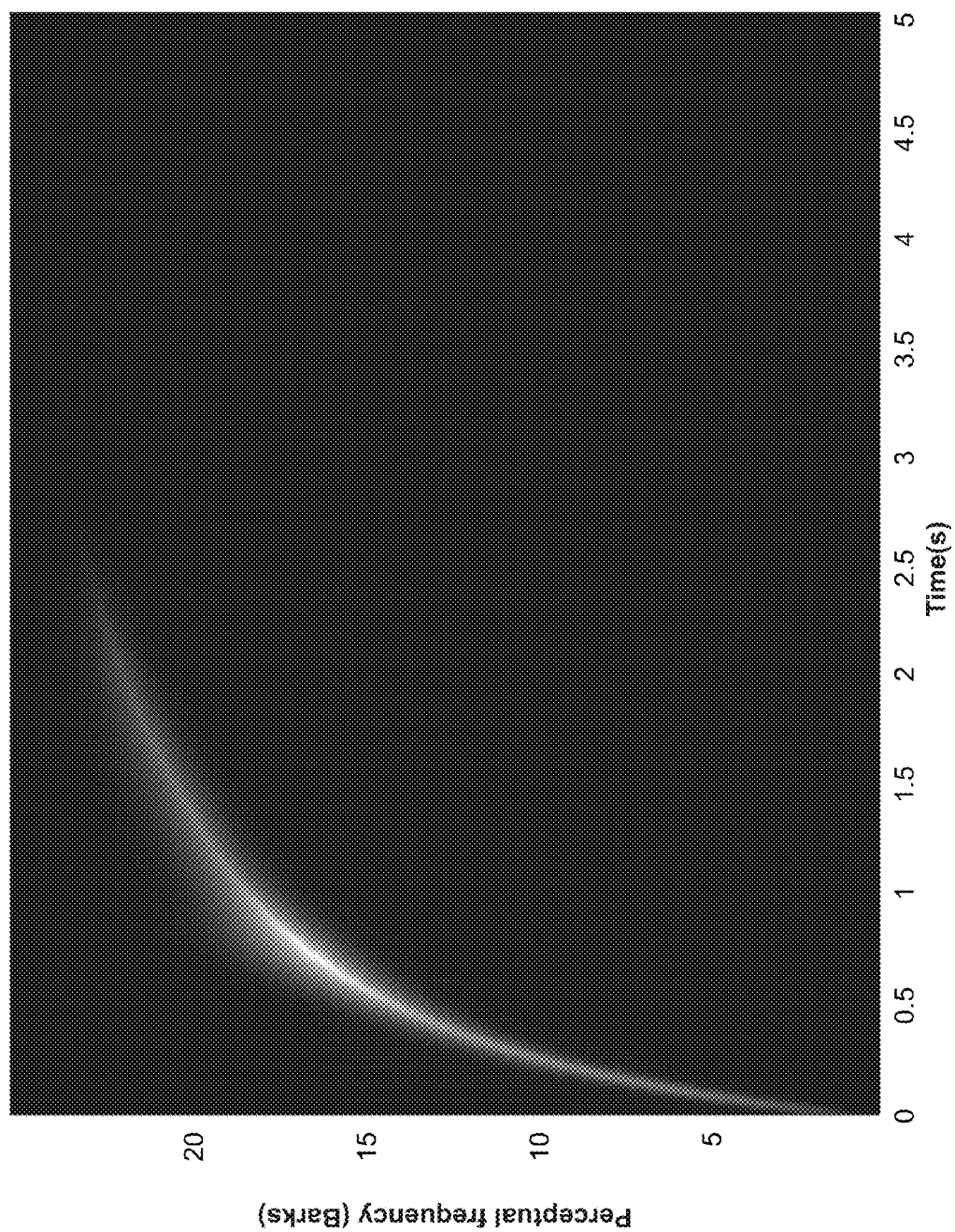
FIG. 6 represents a time-perceptual frequency—perceptual loudness image.

FIG. 6 represents a time-perceptual frequency-perceptual loudness image. The aforementioned embodiments utilize a transformation algorithm that transforms the time domain waveform of FIG. 5 into a time-perceptual frequency-loudness domain as shown in FIG. 6. It should be understood that the transformation algorithm is not based on the short-term DFT, DWT or any other known transformation technique, but utilizes inner products calculation of the segmented signal and complex FIR filter bank impulse responses (IRs), directly representing the Bark scale and critical bands properties. It should also be understood that any non-linear (e.g. "mel" scale) or linear scale can be utilized by the transformation algorithm during the filter-bank construction.

The Bark scale, particularly obtained with regard to Eq. 1 (shown below) has been found to be the closest to the human pitch perception and human auditory system frequency resolution, thus has been exploited in the implementation. The Bark scale is a psychoacoustic scale proposed by Eberhard Zwicker in 1961. It is named after Heinrich Barkhausen who introduced the first subjective measurements of loudness. The scale ranges from 1 to 24 and corresponds to the first 24 critical bands of hearing. The subsequent band edges are (in Hz) 20, 100, 200, 300, 400, 510, 630, 770, 920, 1080, 1270, 1480, 1720, 2000, 2320, 2700, 3150, 3700, 4400, 5300, 6400, 7700, 9500, 12000, 15500.

Typical modeling of Basilar membrane deformation, i.e., modeling psychoacoustic phenomena, is based on a discrete Fourier spectrum with equally spaced frequencies (in Hz) and energy represented by the spectrum bins. Such a model has several limitations, because the spectrum resolution does not represent the resolution of the human hearing. Therefore, it is necessary to chose an appropriate spectrum order (reflecting time vs. frequency resolution), which is achieved by manipulating signal block lengths.

Increasing signal block lengths results in increased frequency resolution (more spectrum bins represent the entire signal frequency range, limited by the Nyquist frequency), but it decreases time domain resolution. For the lower frequency bands, it is desirable to have high frequency domain resolution because humans perceive low frequency sounds with increased resolutions, while high frequency sounds should be represented by decreased frequency domain resolution. Also, the time resolution for different frequencies is not constant, i.e., lower sounds are perceived with lower time domain resolution, and higher pitched sounds are perceived with increased time domain resolution which corresponds with the time domain masking phenomena. It is clear, that using Fourier spectra has several limitations and does not allow for simulating the Basilar membrane deformation changes over time very accurately.

To overcome these limitations, the transformation algorithm is based on a complex numbered filter-bank impulse response directly related to human auditory system resolution. Time domain properties of the impulse responses depend on their center frequencies and bandwidth, i.e., the time domain resolution increases with the increase of the center frequencies of the filters and resembles the resolution of the human auditory system. In order to calculate center frequencies and bandwidth of the filters, the frequency scale is divided into N equally spaced (in Bark units) segments. Recalculation from Hz to Barks is based on the following empirical formula:

$$z = \begin{cases} \frac{26.81 \cdot f}{1960 + f} - 0.53 \\ \text{for } z < 2, z = z + 0.15 \cdot (2 - z) \\ \text{for } z > 20.1, z = z + 0.22 \cdot (z - 20.1) \end{cases} \quad (1)$$

Where:
z—critical band rate,
f—frequency in Hz.

The nth filter bandwidth ranges from $F_z[n-1]$ to $F_z[n+1]$, where $F_z$ represents the frequency (in Hz) of the nth critical band frequency scale segment. The filter IRs can be obtained with any linear phase FIR filter design technique (e.g., with a window-based finite impulse response filter design method, as it is done in the implementation). In addition, each impulse response (k) can be weighted by a width controlled windowing function, such as Gaussian window. Such operation allows for additional control of the time domain performance of each transformation sub-band. The set of impulse responses forms matrix K:

$$K_{re} = \begin{bmatrix} k_n^m & \cdots & k_n^M \\ \vdots & \ddots & \vdots \\ k_N^m & \cdots & k_N^M \end{bmatrix} \quad (2)$$

where:
M—is the IRs length, equal to processed signal segments length,
N—number of sub-bands (frequency resolution of the representation)
$K_{im}$—imaginary part of the matrix $K_{re}$ is obtained with the use of Hilbert transform and both $K_{re}$ and $K_{im}$ are used to form complex impulse responses matrix K. The complex representation, with perceptually spaced frequency domain (i.e. equally spaced in Bark units), is calculated with the inner product operations:

$$P_t = K \cdot s_t \quad (3)$$

where:
$P_t$—the invented complex representation at instance t (for tth processing block)
K—complex filter impulse response matrix,
$s_t$—tth input signal segment.

Outer-middle ear frequency characteristics are simulated with accordance to the following formula and are used to weight each representation band:

$$A = -0.6 \cdot 3.64 \cdot f^{-0.8} + 6.5 \cdot e^{-0.6 \cdot (f - 3.3)^2} - 10^{-3} \cdot f^4 \quad (4)$$

Based on the representation P (calculated with Eq. 3) it is possible to simulate the simultaneous masking phenomena and calculate Basilar membrane deformation curve. The simulation is performed similarly as with the use of complex Fourier spectrum. In the first step, tonality descriptors of the representation components are calculated. The tonality is represented by the Unpredictability Measure (UM) parameter and further used for calculating the masking offset. The offset for the excitation of $b_x$ Barks at frequency of $b_x$ Barks is given by the formula:

$$O_{k,x} = \alpha_k^t \cdot (14.5 + \text{bark}(x)) + (1 - \alpha_k^t) \cdot 5.5 \quad (5)$$

The tonality index $\alpha_k^t$ of excitation of $b_x$ Barks is represented by the UM parameter ($\alpha_k^t = c_k^t$), where $c_k^t$ is calculated in the following way:

$$c_k^t = \frac{\sqrt{(r_k^t \cdot \cos\Phi_k^t - \hat{r}_k^t \cdot \cos\hat{\Phi}_k^t)^2 + (r_k^t \cdot \sin\Phi_k^t - \hat{r}_k^t \cdot \sin\hat{\Phi}_k^t)^2}}{r_k^t - |\hat{r}_k^t|} \quad (6)$$

For $r_k^t$ denoting spectral magnitude and $\Phi_k^t$ denoting phase, both at time t, while $\hat{r}_k^t$ and $\hat{\Phi}_k^t$ represent the predicted values of $\Phi_k^t$, and are referred to the past information (calculated for two previous signal segments):

$$\alpha_k^t = \begin{cases} \hat{r}_k^t = r_k^{t-1} + (r_k^{t-1} - r_k^{t-2}) \\ \hat{\Phi}_k^t = \Phi_k^{t-1} + (\Phi_k^{t-1} - \Phi_k^{t-2}) \end{cases} \Rightarrow \begin{cases} \hat{r}_k^t = 2 \cdot r_k^{t-1} - r_k^{t-2} \\ \hat{\Phi}_k^t = 2 \cdot \Phi_k^{t-1} - \Phi_k^{t-2} \end{cases} \quad (7)$$

Phase prediction is possible due to the complex numbered character of the representation (P from Eq. 3). The masking threshold T of the Basilar membrane, stimulated by a single tone excitation of $b_x$ Barks of magnitude equal to $S_x$ is calculated with regard to the formula:

$$\begin{cases} T_{i,x} = P_i \cdot 10^{-P_1 \cdot (b_x - b_i)/10 - O_{i,x}}, & b_x \leq b_i \\ T_{j,x} = P_j \cdot 10^{-P_2 \cdot (b_j - b_x)/10 - O_{j i,x}}, & b_x > b_j \end{cases} \quad (8)$$

And the global masking threshold at $b_x$ Barks is:

$$T_x = \sum_{j \in J} T_{j,x} + \sum_{i \in I} T_{i,x} \quad (9)$$

FIG. 6 shows a representation of the same signal of FIG. 5, however with the use of the transformation algorithm (Eq. 3) and perceptual masking modeling (Eq. 4-9). As shown in FIG. 6, the perceptual frequency of the chirp signal increases rapidly for lower frequencies and the increase slows down for higher perceptual frequency band. Also, it can be observed that the maximum loudness level is reached at 0.7 s (for 17 barks, i.e. around 2 kHz), which is indicated by white color, while below 1 Bark and above 24 Barks loudness is near zero. The loudness curve L (without the frequency domain properties) is achieved, by averaging energy (RMS) of each column of the psychoacoustic representation (matrix) T:

$$L_m = \sqrt{\frac{1}{N} \sum_{n=1}^{N} T_{n,m}^2} \quad (10)$$

Where N denotes number of subbands (see also Eq. 2).

Figure 7:
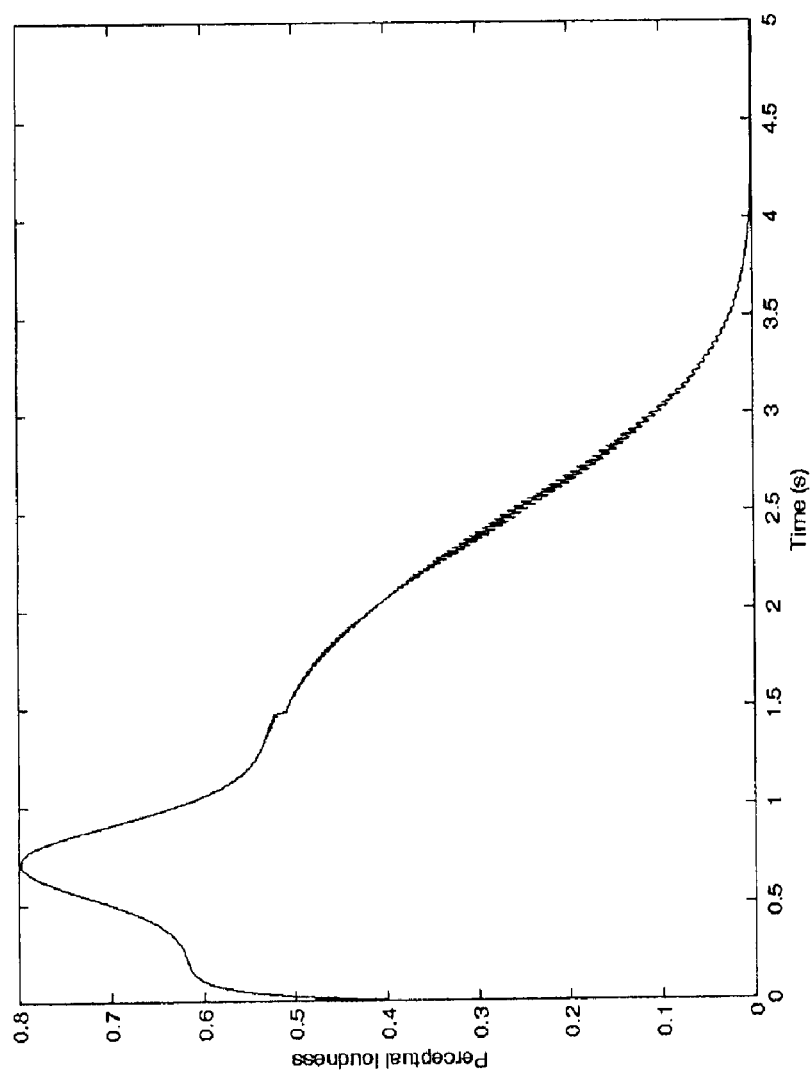
FIG. 7 represents a loudness contour of a chirp signal.

FIG. 7 represents a loudness contour of the chirp signal. It can be observed that it reaches its maximum value at 0.7 seconds, which corresponds to image in of FIG. 6.

Additionally, the transformation algorithm contains a set of auxiliary algorithms for automated analysis of the psychoacoustic representation. The algorithms are responsible for simulating periodicity perception of the acoustic events, since humans have ability to concentrate their attention on repetitive events (rhythmic events such as heart beats, murmurs, etc.) and rejecting incidental events, which usually are parasite disturbances. The periodicity analysis can be utilized to detect cardiac cycle periods based on the T representation, however for reducing the computational complexity it is possible to utilize the loudness curve L only, or combine both (i.e. periodicity detection with L and periods averaging in T). The periods lengths are obtained by comparing segments of the representation with other segments offset by a trial period to find a match, similarly as it is done in the pitch detection algorithms operating in the time domain. Average magnitude difference function (AMDF) or the similar autocorrelation are used for this purpose:

Autocorrelation:

$$\alpha_t(t) = \frac{\sum_{n=-N/2}^{N/2-1} x(t+n) \cdot x(t+n-P)}{\sqrt{\sum_{n=-N/2}^{N/2-1} x^2(t+n) \cdot \sum_{n=N/2}^{N/2-1} x^2(t+n+P)}} \quad (11)$$

AMDF:

$$\gamma_t(t) = \sum_{n=N/2}^{N/2-1} |x(n+m) \cdot w(m) - x(n+m-t) \cdot w(m-t)| \quad (12)$$

where:
α—autocorrelation signal,
γ—AMDF signal,
w—weighting window function (e.g. Hann's, Kaiser's, etc.)

In case of periodicity analysis of the time-perceptual frequency-loudness representation, above algorithms (Eq. 11-12) are applied for each row of the matrix T independently.

The transformation algorithm allows for calculating psychoacoustic auscultation sound representation, which is visualization of the basilar membrane deformation changes over time (tth column of matrix T, representing tth signal block is the basilar membrane deformation at time instant t). Further, the auscultation signal findings are described in terms of perception of the acoustical phenomena. Therefore, audible events can be observed in a psychoacoustic representation image, and inaudible events cannot (which is not always the case in phonocardiographic, or other non-psychoacoustic representations), thereby allowing for utilizing the representation for supporting physicians during the auscultation procedure. The transformation algorithm further allows physicians to utilize the existing descriptive auscultation knowledge, gathered over nearly 200 years. Furthermore, the transformation algorithm allows for objectification of the examination because the sense of sight is far better developed among humans, than the sense of hearing. Such a representation also allows for automated analysis of the acoustic signal, for the data (images) exchange and consultations.

Figure 8:
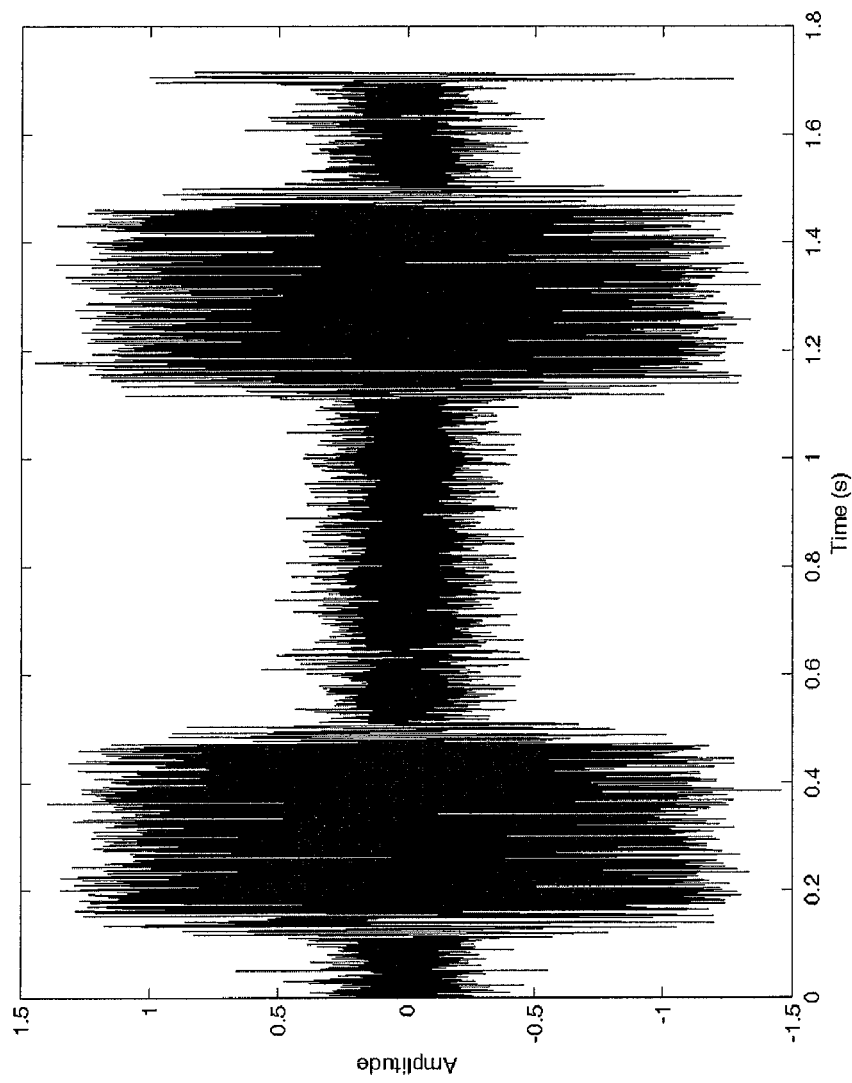
FIG. 8 represents a phonocardiographic representation (time domain waveform) of a cardiac auscultation signal with a holosystolic murmur.

FIG. 8 represents a phonocardiographic representation (time domain waveform) of a cardiac auscultation signal with a holosystolic murmur (lasting from S1 to S2—see FIG. 1) with an additional S3 sound. When carefully listening to the signal, S1, S2 and S3 are audible. The holosystolic murmur is loud and easy to detect. The recording is poor quality and very noisy, thus S3 is obscured by noise and not visible in the phonocardiographic representation. Moreover, S1 and S2 are obscured by the holosystolic murmur, and cannot be observed in the waveform either.

Figure 9:
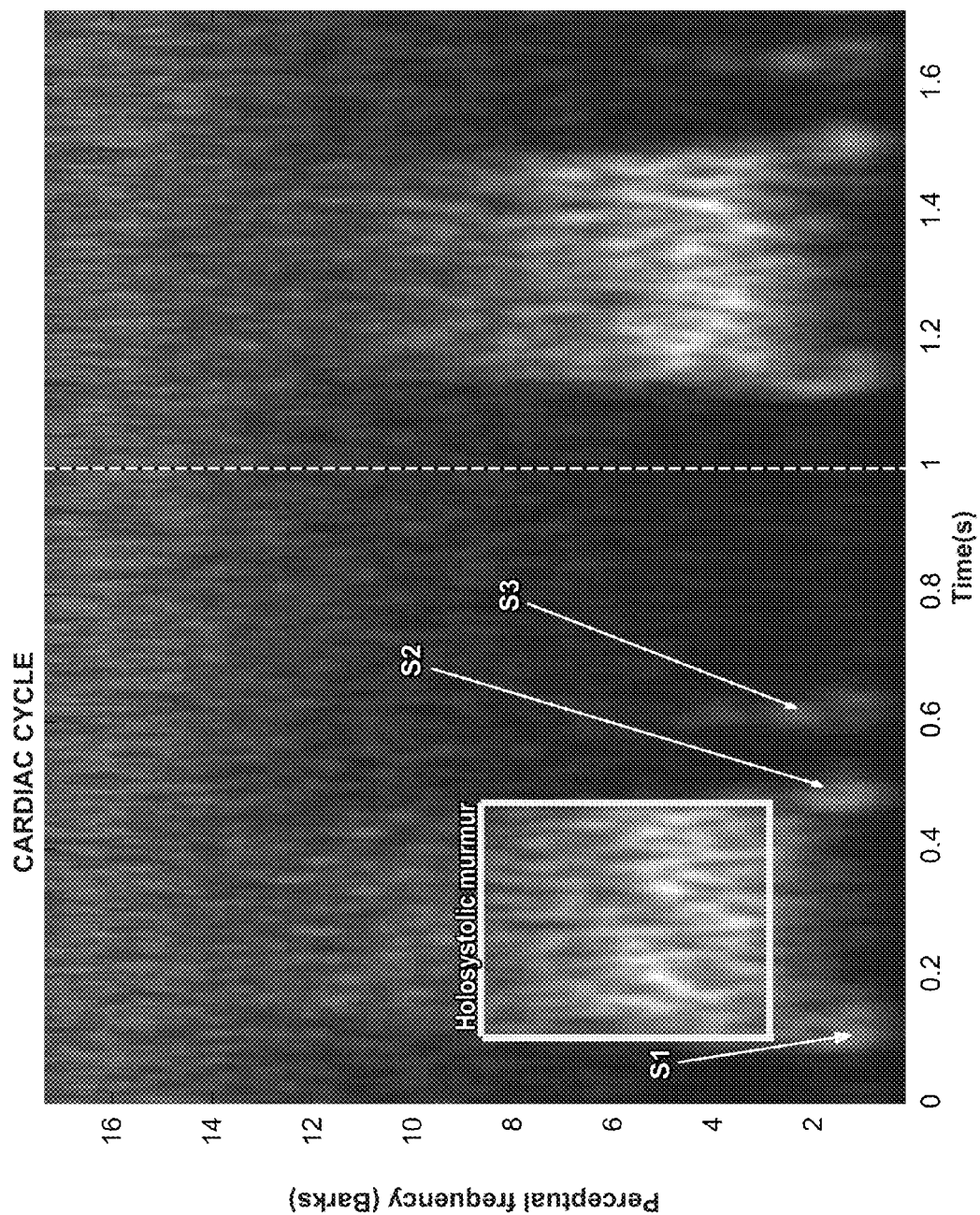
FIG. 9 represents a psychoacoustic time-perceptual frequency-perceptual loudness of the same signal of FIG. 8.

FIG. 9 represents a psychoacoustic time-perceptual frequency-loudness of the same signal of FIG. 8 determined by the above-mentioned transformation algorithm. It can be observed that S1 and S2 are easily distinguishable from the holosystolic murmur because they have significantly lower frequencies. Further, S3 is visible in the image, and is distinguishable from the background high frequency noise.

Figure 10:
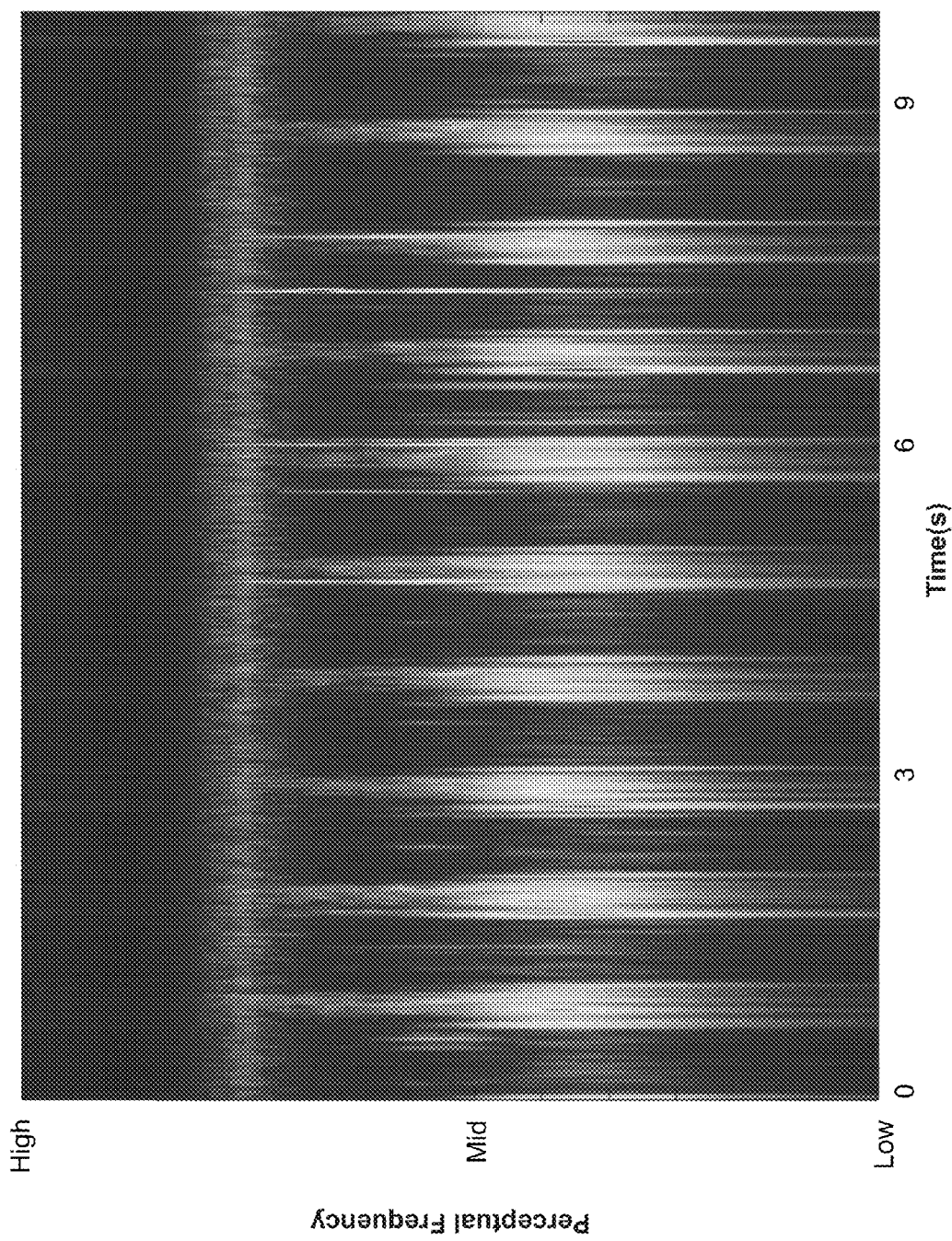
FIG. 10 shows an example of a time-perceptual frequency-perceptual loudness domain representation of a cardio-acoustic signal.

FIG. 10 shows an example of the time-perceptual frequency-perceptual loudness domain representation, i.e., basilar membrane shape changes over time. In the representation of an certain cardio-acoustic signal, impulsive events (such as heart beats or clicks) are visible as vertical shapes of short duration, while long lasting murmurs are visible as frequency limited with relatively high center frequency shapes of longer duration.

Figure 11:
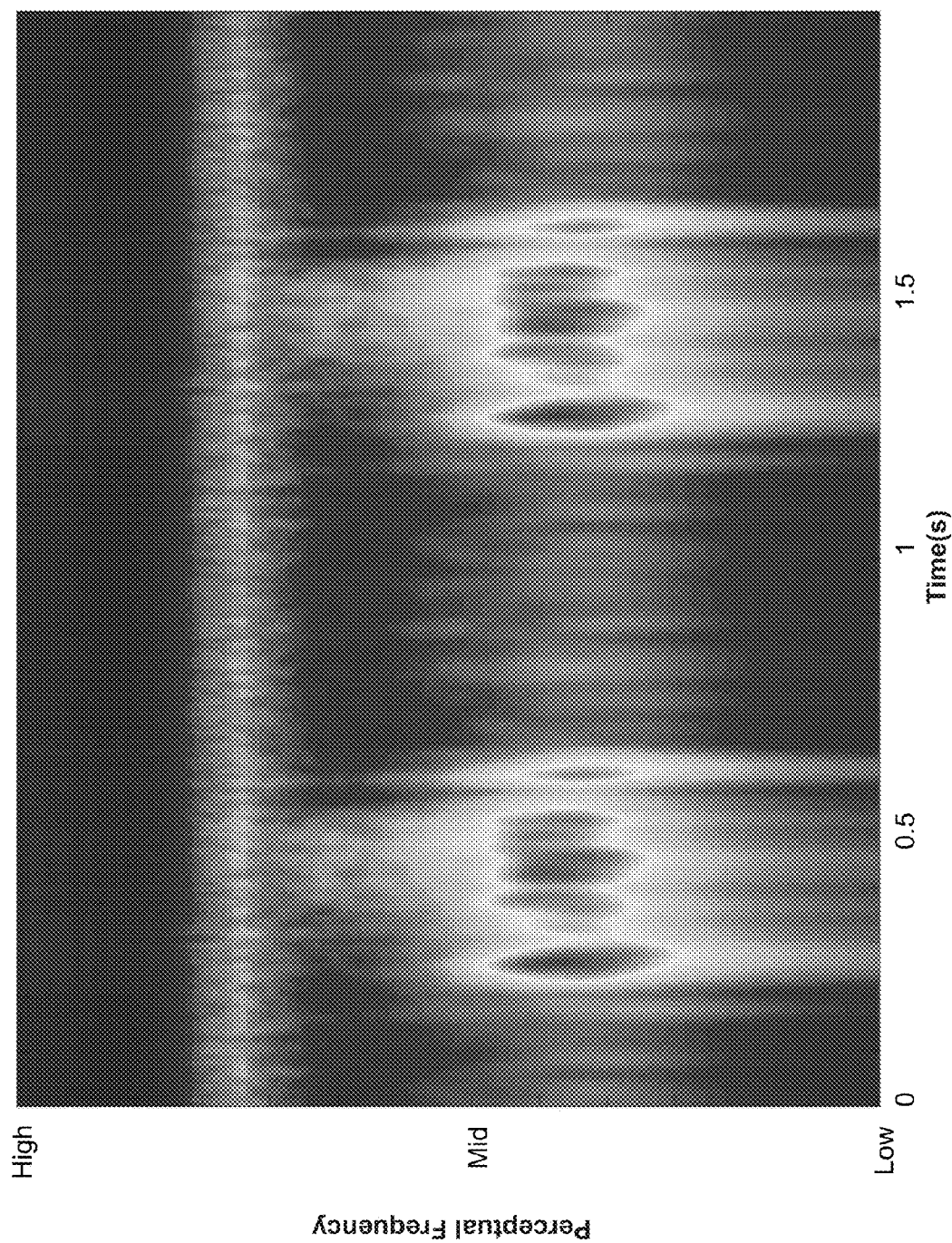
FIG. 11 represents a stimulation of an ability of a human listener, with the use of the same signal of FIG. 10.

FIG. 11 represents a simulation of the pattern tracking ability of a human listener, with the use of the same cardio-acoustic signal of FIG. 10. It can be observed that the representation is much smoother than the one showed in FIG. 10 with repetitive events emphasized.

Figure 12:
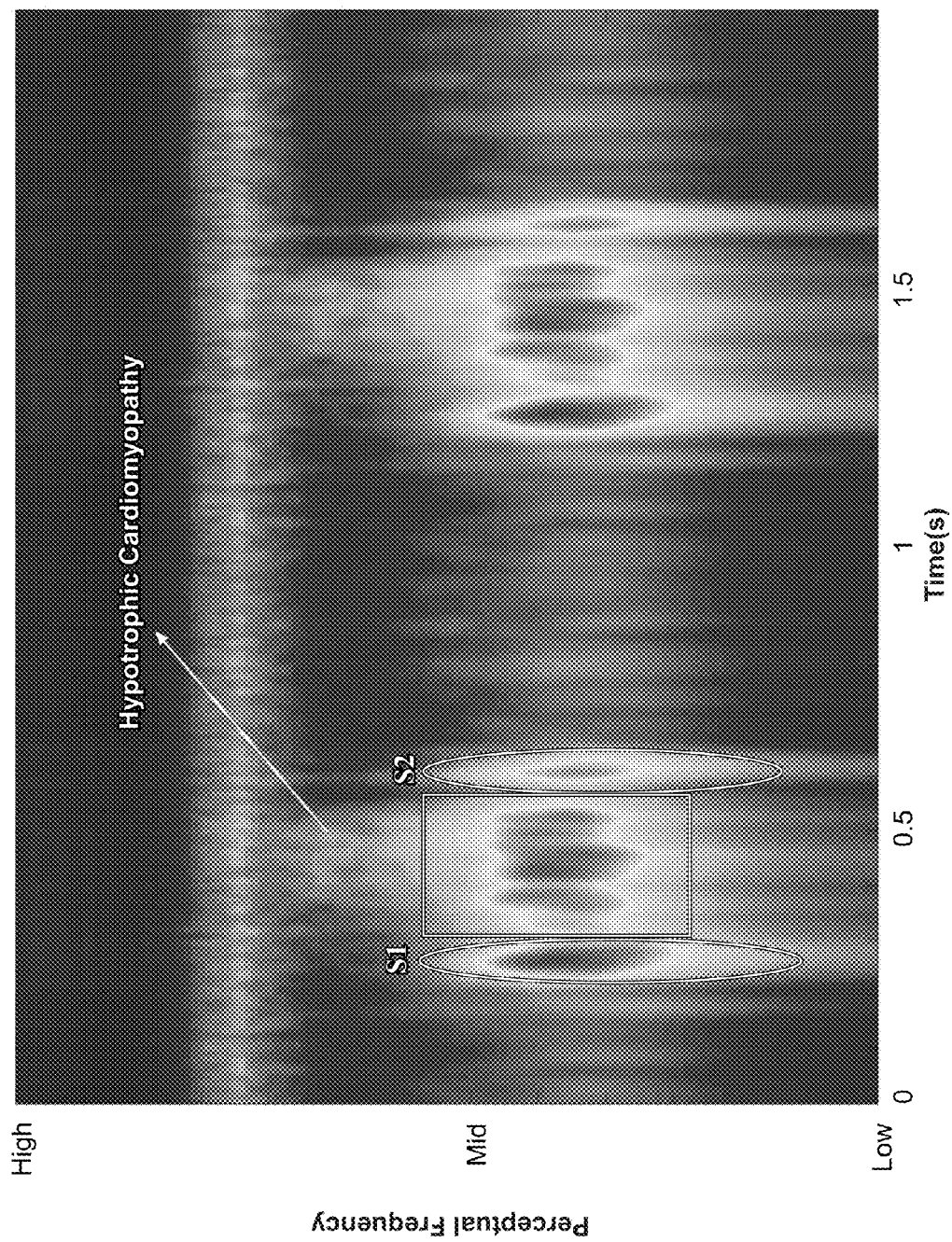
FIG. 12 illustrates an example of auscultatory findings detected by a transformation algorithm.

FIG. 12 illustrates an example of the auscultatory findings detected in the signal of FIG. 11. In this example, the cardio-acoustic signal may be interpreted as indicative hypertrophic cardiomyopathy.

The transformation algorithm provides the use of human auditory system modeling application for analysis of auscultation acoustic signal, which could be implemented on various computers or other devices, with regard to specific requirements and knowledge of the users. The innovation is based on the algorithm (could be viewed as a DSP hardware device with dedicated DSP chip), which transforms the time domain waveform into the time—perceptual frequency—perceptual loudness domain.

The above-described systems and methods can be implemented in digital electronic circuitry, in computer hardware, firmware, and/or software. The implementation can be as a computer program product (i.e., a computer program tangibly embodied in an information carrier). The implementation can, for example, be in a machine-readable storage device and/or in a propagated signal, for execution by, or to control the operation of, data processing apparatus. The implementation can, for example, be a programmable processor, a computer, and/or multiple computers.

A computer program can be written in any form of programming language, including compiled and/or interpreted languages, and the computer program can be deployed in any form, including as a stand-alone program or as a subroutine, element, and/or other unit suitable for use in a computing environment. A computer program can be deployed to be executed on one computer or on multiple computers at one site.

Method steps can be performed by one or more programmable processors executing a computer program to perform functions of the invention by operating on input data and generating output. Method steps can also be performed by and an apparatus can be implemented as special purpose logic circuitry. The circuitry can, for example, be a FPGA (field programmable gate array) and/or an ASIC (application-specific integrated circuit). Modules, subroutines, and software agents can refer to portions of the computer program, the processor, the special circuitry, software, and/or hardware that implements that functionality.

Processors suitable for the execution of a computer program include, by way of example, both general and special purpose microprocessors, and any one or more processors of any kind of digital computer. Generally, a processor receives instructions and data from a read-only memory or a random access memory or both. The essential elements of a computer are a processor for executing instructions and one or more memory devices for storing instructions and data. Generally, a computer can include, can be operatively coupled to receive data from and/or transfer data to one or more mass storage devices for storing data (e.g., magnetic, magneto-optical disks, or optical disks).

Data transmission and instructions can also occur over a communications network. Information carriers suitable for embodying computer program instructions and data include all forms of non-volatile memory, including by way of example semiconductor memory devices. The information carriers can, for example, be EPROM, EEPROM, flash memory devices, magnetic disks, internal hard disks, removable disks, magneto-optical disks, CD-ROM, and/or DVD-ROM disks. The processor and the memory can be supplemented by, and/or incorporated in special purpose logic circuitry.

To provide for interaction with a user, the above described techniques can be implemented on a computer having a display device. The display device can, for example, be a cathode ray tube (CRT) and/or a liquid crystal display (LCD) monitor. The interaction with a user can, for example, be a display of information to the user and a keyboard and a pointing device (e.g., a mouse or a trackball) by which the user can provide input to the computer (e.g., interact with a user interface element). Other kinds of devices can be used to provide for interaction with a user. Other devices can, for example, be feedback provided to the user in any form of sensory feedback (e.g., visual feedback, auditory feedback, or tactile feedback). Input from the user can, for example, be received in any form, including acoustic, speech, and/or tactile input.

The above described techniques can be implemented in a distributed computing system that includes a back-end component. The back-end component can, for example, be a data server, a middleware component, and/or an application server. The above described techniques can be implemented in a distributing computing system that includes a front-end component. The front-end component can, for example, be a client computer having a graphical user interface, a Web browser through which a user can interact with an example implementation, and/or other graphical user interfaces for a transmitting device. The components of the system can be interconnected by any form or medium of digital data communication (e.g., a communication network). Examples of communication networks include a local area network (LAN), a wide area network (WAN), the Internet, wired networks, and/or wireless networks.

The system can include clients and servers. A client and a server are generally remote from each other and typically interact through a communication network. The relationship of client and server arises by virtue of computer programs running on the respective computers and having a client-server relationship to each other.

Packet-based networks can include, for example, the Internet, a carrier internet protocol (IP) network (e.g., local area network (LAN), wide area network (WAN), campus area network (CAN), metropolitan area network (MAN), home area network (HAN)), a private IP network, an IP private branch exchange (IPBX), a wireless network (e.g., radio access network (RAN), 802.11 network, 802.16 network, general packet radio service (GPRS) network, HiperLAN), and/or other packet-based networks. Circuit-based networks can include, for example, the public switched telephone network (PSTN), a private branch exchange (PBX), a wireless network (e.g., RAN, bluetooth, code-division multiple access (CDMA) network, time division multiple access (TDMA) network, global system for mobile communications (GSM) network), and/or other circuit-based networks.

The transmitting device can include, for example, a computer, a computer with a browser device, a telephone, an IP phone, a mobile device (e.g., cellular phone, personal digital assistant (PDA) device, laptop computer, electronic mail device), and/or other communication devices. The browser device includes, for example, a computer (e.g., desktop computer, laptop computer) with a world wide web browser (e.g., Microsoft® Internet Explorer® available from Microsoft Corporation, Mozilla® Firefox available from Mozilla Corporation). The mobile computing device includes, for example, a Blackberry®.

Comprise, include, and/or plural forms of each are open ended and include the listed parts and can include additional parts that are not listed. And/or is open ended and includes one or more of the listed parts and combinations of the listed parts.

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

What is claimed is:

1. A method for cardio-acoustic signal analysis, comprising:
   receiving, via a signal receiver, a signal representative of heart sounds;
   transforming, via a processing unit, the received signal to represent a time, perceptual-frequency, amplitude domain;
   applying, via the processing unit, a human auditory system modeling algorithm to the time, perceptual frequency, amplitude domain representation to generate a time, perceptual-frequency, perceptual-loudness domain representation; and
   displaying, via a visualization unit, the received signal in the time, perceptual-frequency, perceptual-loudness domain representation.

2. The method of claim 1, wherein the transformation is based on inner product calculations using a finite impulse response (FIR) filter bank representing a non-linear frequency resolution.

3. The method of claim 2, wherein the finite impulse response filter bank is complex numbered and represents properties of perceptual-frequency characteristics.

4. The method of claim 3, wherein the perceptual-frequency characteristics correspond to critical bands of hearing and represent a Bark frequency scale.

5. The method of claim 3, wherein the complex numbered impulse responses filter bank allow for calculating phase prediction and amplitude prediction of spectral components.

6. The method of claim 5, further comprising calculating, via the processing unit, tonality using an unpredictability measure parameter.

7. The method of claim 6, further comprising distinguishing, via the processing unit, between noisy and tonal components in the received signal.

8. The method of claim 7, further comprising simulating, via the processing unit, periodicity perception of the received signal.

9. The method of claim 1, further comprising interpreting, via the processing unit, the time, perceptual-frequency, perceptual-loudness domain representation for cardio-acoustic signal analysis.

10. The method of claim 9, wherein interpreting the time-perceptual frequency-perceptual loudness domain representation includes comparing, via the processing unit, the time, perceptual-frequency, perceptual-loudness domain representation to a perceived acoustical phenomena.

11. The method of claim 1, wherein the received signal is representative of at least cardiac auscultation and pulmonary auscultation.

12. The method of claim 1, further comprising applying, via the processing unit, periodicity analysis methods to the time, perceptual-frequency, perceptual-loudness domain representation.

13. The method of claim 12, further comprising detecting, via the processing unit, S1 and S2 of at least 2 cardiac cycles for calculating an averaged cardiac cycle representation.

14. The method of claim 13, further comprising limiting, via the processing unit, influence of noise and other non-repetitive parasite artifacts and disturbances to the received signal.

15. The method of claim 13, further comprising restoring, via the processing unit, the cardiac auscultation signal to remove noise, parasite clicks, or any combination thereof.

16. The method of claim 1, wherein the applying the human auditory system modeling algorithm simulates psychoacoustic masking phenomena.

17. A system for cardio-acoustic signal analysis, comprising:
   an input sensor for receiving a signal representative of heart sounds;
   a transformation module for transforming the receive signal to represent a time, perceptual-frequency, perceptual-loudness domain; and
   a display device for displaying the received signal in the time, perceptual-frequency, perceptual-loudness domain.

18. A system for cardio-acoustic signal analysis, comprising:
   means for receiving a signal representative of heart sounds;
   means for transforming the received signal to represent a time, perceptual-frequency, perceptual-loudness domain; and
   means for displaying the received signal in a time, perceptual-frequency, perceptual-loudness domain representation.

* * * * *